(12) United States Patent
Hsieh et al.

(10) Patent No.: US 7,627,078 B2
(45) Date of Patent: *Dec. 1, 2009

(54) METHODS AND APPARATUS FOR DETECTING STRUCTURAL, PERFUSION, AND FUNCTIONAL ABNORMALITIES

(75) Inventors: Jiang Hsieh, Brookfield, WI (US); Ricardo Scott Avila, Clifton Park, NY (US); Maria Iatrou, Clifton Park, NY (US); Shankara B. Reddy, Cedarburg, WI (US); Peter Michael Edic, Albany, NY (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 365 days.

This patent is subject to a terminal disclaimer.

(21) Appl. No.: 10/065,689

(22) Filed: Nov. 8, 2002

(65) Prior Publication Data

US 2004/0092814 A1    May 13, 2004

(51) Int. Cl.
*G01N 23/00* (2006.01)

(52) U.S. Cl. ............... 378/4; 378/5; 378/19; 378/98.9; 378/901; 382/128; 382/130; 382/131; 382/132; 600/407; 600/425

(58) Field of Classification Search .............. 378/4, 378/5, 8, 9, 15, 20, 62, 94, 119, 138, 19; 600/407, 410, 504, 544, 424, 425, 436, 420; 382/131
See application file for complete search history.

(56) References Cited

U.S. PATENT DOCUMENTS

| | | | |
|---|---|---|---|
| 4,361,901 A | 11/1982 | Daniels et al. | |
| 5,269,315 A * | 12/1993 | Leuchter et al. | 600/544 |
| 5,570,403 A | 10/1996 | Yamazaki et al. | |
| 5,665,971 A | 9/1997 | Chen et al. | |
| 6,018,562 A * | 1/2000 | Willson | 378/9 |
| 6,185,272 B1 | 2/2001 | Hiraoglu et al. | |
| 6,236,709 B1 | 5/2001 | Perry et al. | |
| 6,320,931 B1 | 11/2001 | Arnold | |
| 6,369,389 B1 | 4/2002 | Berlad et al. | |
| 6,399,951 B1 * | 6/2002 | Paulus et al. | 250/370.13 |
| 6,490,476 B1 * | 12/2002 | Townsend et al. | 600/427 |
| 6,507,633 B1 | 1/2003 | Elbakri et al. | |
| 6,560,315 B1 | 5/2003 | Price et al. | |
| 6,687,333 B2 * | 2/2004 | Carroll et al. | 378/119 |
| 6,754,298 B2 * | 6/2004 | Fessler | 378/4 |
| 6,792,302 B2 * | 9/2004 | Wintermark et al. | 600/407 |
| 6,898,263 B2 * | 5/2005 | Avinash et al. | 378/4 |
| 6,999,549 B2 * | 2/2006 | Sabol et al. | 378/5 |
| 7,058,155 B2 * | 6/2006 | Piacsek et al. | 378/4 |
| 7,272,429 B2 * | 9/2007 | Walker et al. | 600/407 |
| 2002/0163988 A1 | 11/2002 | Nisius et al. | |
| 2003/0063787 A1 | 4/2003 | Natanzon et al. | |
| 2004/0102688 A1 * | 5/2004 | Walker et al. | 600/407 |

* cited by examiner

*Primary Examiner*—Brian Casler
*Assistant Examiner*—Baisakhi Roy
(74) *Attorney, Agent, or Firm*—Armstrong Teasdale LLP

(57) ABSTRACT

A Multi-Energy Computed Tomography (MECT) System is provided. The system includes a radiation source rotatable about a patient, a radiation detector, and a computer coupled to the radiation source and the radiation detector wherein the computer is configured to receive data regarding a first energy spectrum of a scan of a head of the patient, receive data regarding a second energy spectrum of a scan of the head, and generate an image using the received data.

31 Claims, 1 Drawing Sheet

METHODS AND APPARATUS FOR DETECTING STRUCTURAL, PERFUSION, AND FUNCTIONAL ABNORMALITIES

BACKGROUND OF INVENTION

This invention relates to computed tomographic (CT) imaging, and more particularly to methods and apparatus for the detection and diagnosis of head and neck abnormalities.

In spite of recent advancements in CT technology (faster scanning speed, larger coverage with multiple detector rows), energy resolution is still a missing piece, namely, wide x-ray photon energy spectrum from the x-ray source and the lack of energy resolution from CT detection systems. X-ray attenuation through a given object is not a constant. Rather the X-ray attenuation is strongly dependent on the x-ray photon energy. This physical phenomenon shows in the image as beam-hardening artifact, such as, for example, non-uniformity, shading and streaks. Some of the beam-hardening artifacts can be easily corrected, but some beam-hardening artifacts are more difficult to remove (i.e., correct). In general, known methods to deal with such problems include (1) water calibration, where each CT machine is carefully calibrated to remove beam hardening from materials similar to water, and (2) iterative bone correction, where bones are separated in the first-pass image, then beam hardening from bones are corrected in the second-pass. However, beam hardening from materials other than water and bone, such as metal and contrast agent, may be difficult to correct. Also, even with the above described correction methods, conventional CT does not provide quantitative image values, instead, the same material at different locations often shows different CT numbers.

Another drawback of conventional CT is a lack of material characterization. For example, a highly attenuating material with a low density can result in the same CT number in the image as a less attenuating material with a high density. Thus, there is little or no insight into what a material is made of based solely on the CT number. At least some state-of-the-art CT scanner currently available is limited to providing anatomical information. For head and neck scans, images produced by such scanners exhibit a significant level of image artifacts and CT number inaccuracy. These limitations prevent the utilization of the CT device for advanced diagnosis. Accordingly, the methods and apparatus described herein address the detection and diagnosis of head and neck abnormalities.

SUMMARY OF INVENTION

In one aspect, a method for obtaining data is provided. The method includes scanning at least one of a head of a patient and a neck of the patient with a Multi-Energy Computed Tomography (MECT) system to acquire data.

In another aspect, a Multi-Energy Computed Tomography (MECT) System is provided. The MECT includes a radiation source, a radiation detector, and a computer coupled to the radiation source and the radiation detector. The computer is configured to receive data regarding a first energy spectrum of a scan of a head of a patient, receive data regarding a second energy spectrum of a scan of the head, and generate an image of at least one of a cerebral blood volume of the patient and a cerebral blood flow of the patient.

In yet another aspect, a Multi-Energy Computed Tomography (MECT) System is provided. The MECT includes a radiation source, a radiation detector, and a computer coupled to the radiation source and the radiation detector. The computer is configured to receive data regarding a first energy spectrum of a scan of at least one of a head of a patient and a neck of the patient, receive data regarding a second energy spectrum of the scan, and generate a location of a tagging ligand based upon the received data.

In still another aspect, a Multi-Energy Computed Tomography (MECT) System is provided. The MECT includes a radiation source, a radiation detector, and a computer coupled to the radiation source and the radiation detector. The computer is configured to receive data regarding a first energy spectrum of a scan of at least one of a head of a patient and a neck of the patient, receive data regarding a second energy spectrum of the scan, and detect a labeled drug based upon the received data.

In another aspect, a Multi-Energy Computed Tomography (MECT) System is provided. The MECT includes a radiation source, a radiation detector, and a computer coupled to the radiation source and the radiation detector. The computer is configured to receive data regarding a first energy spectrum of a scan of a head of a patient, receive data regarding a second energy spectrum of the scan, generate a location of a tagged ligand with an affinity to a neurotransmitter released by a specific labeled drug's receptors based upon the received data, and detect a labeled drug based upon the received data to simultaneously monitor the labeled drug's distribution and the concentration of the neurotransmitter.

DETAILED DESCRIPTION

Figure 1:
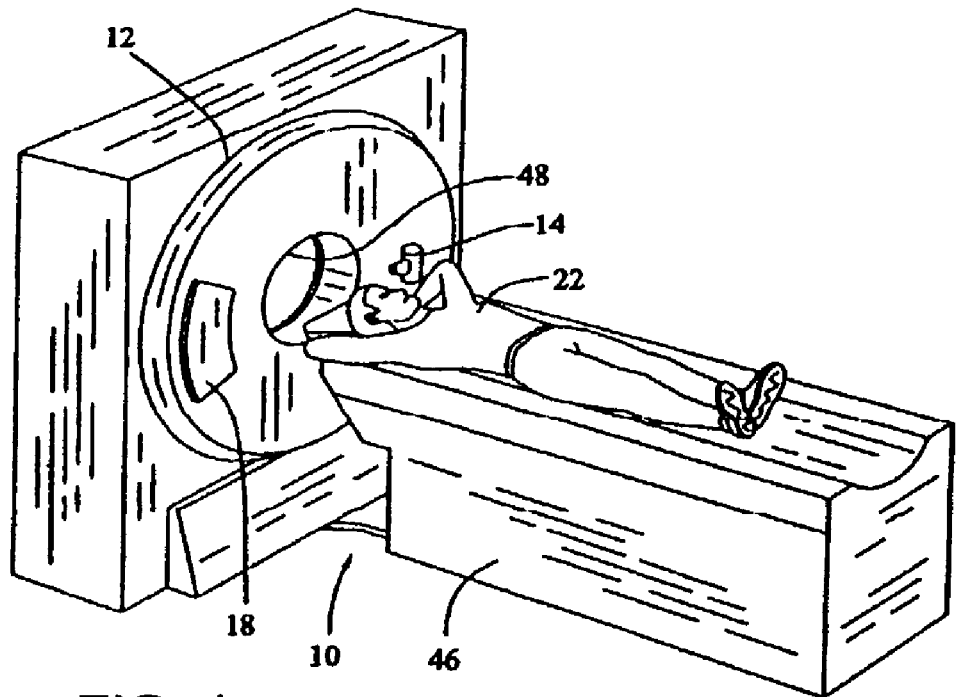
FIG. 1 is a pictorial view of a MECT imaging system.

The methods and apparatus described herein address the detection and diagnosis of abnormalities in the head and neck regions of a patient by employing novel approaches that make use of basic properties of the x-ray and material interaction. For each ray trajectory, multiple measurements with different mean x-ray energies are acquired. As explained in greater detail below, when Basis Material Decomposition (BMD) and Compton and photoelectric decomposition are performed on these measurements, additional information is obtained that enables improved accuracy and characterization.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes.

A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a helical scan may be performed. To perform a helical scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Herein are described methods and apparatus for detecting structural, perfusion and functional abnormalities in head and neck tissue and bone using an energy-discriminating (also known as multi-energy) computed tomography (MECT) system. First described is MECT system 10 and followed by head and neck applications using MECT system 10.

Figure 2:
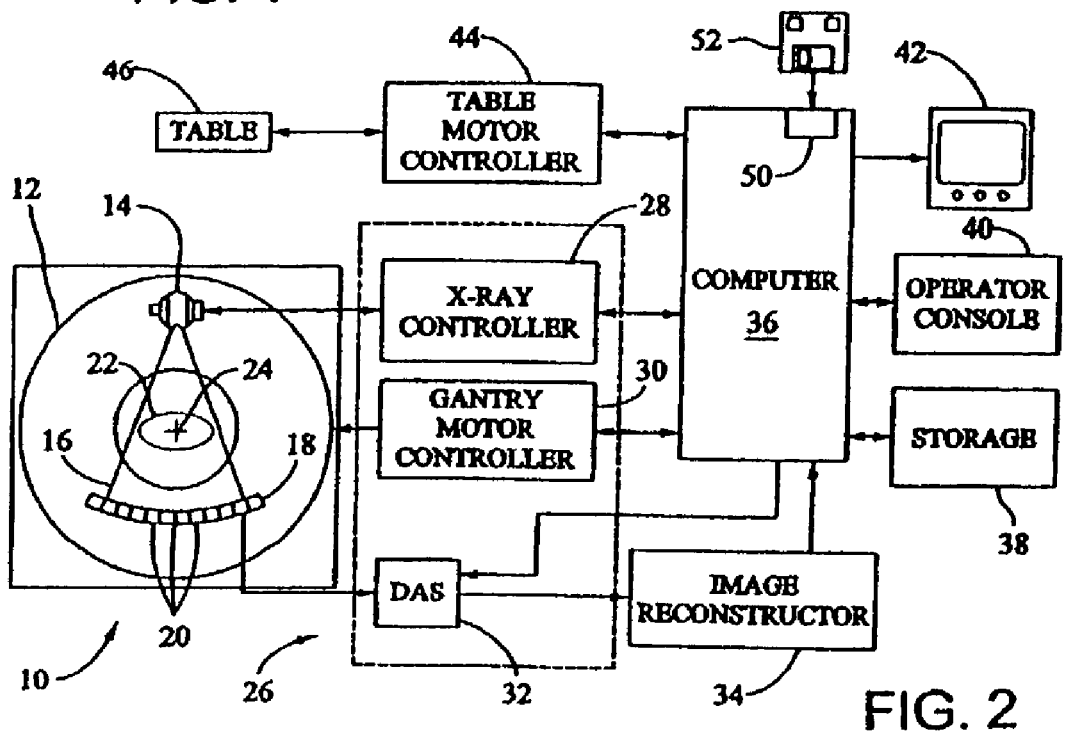
FIG. 2 is a block schematic diagram of the system illustrated in FIG. 1.

Energy Discrimination (multi-energy) CT system 10 Referring to FIGS. 1 and 2, a Multi-Energy multi-slice scanning imaging system, for example, a Multi-Energy computed tomography (MECT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomography (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials, for example. Alternatively, special filters are placed between the x-ray source and the detector such that different detector rows collect projections of different x-ray energy spectrum. Alternatively, the special filters that shape the x-ray spectrum can be used for two scans that are acquired either back to back or interleaved. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source).

Energy Discrimination CT (MECT) can lessen or eliminate the problems associated with conventional CT (lack of energy discrimination and material characterization) altogether. In the absence of object scatter, one only need system 10 to separately detect two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation: (1) Compton scatter and the (2) Photoelectric effect. In order to characterize the behavior of an object under x-ray attenuation, one only need to measure two independent parameters. Thus, detected signals from two energy regions provide enough information that we can use to resolve the energy dependence of the object being imaged.

The data analysis used in MECT includes Compton and photoelectric decomposition: Instead of obtaining an overall attenuation coefficient as in conventional CT images, a pair of images is obtained with MECT 10, separately presenting attenuations from Compton and photoelectric processes. Also, a slight modification in the algorithm can result in images representing effective Z and density.

Basis material decomposition (BMD): This method is based on the concept that the x-ray attenuation (in the energy region for medical CT) of any given material can be represented by proper density mix of other two given materials. These two materials are called the Basis Materials. Through BMD, two CT images can be obtained, each presenting the equivalent density of one of the basis materials. Since density is independent of x-ray photon energy, these images are naturally free of beam-hardening artifacts. Meanwhile, one has the choice of choosing the basis material to target a certain material of interest, thus enhancing the image contrast.

It should be noted that in order to optimize a multi-energy CT system, the larger the spectra separation, the better the image quality. Also, the photon statistics in these two energy regions needs to be similar, otherwise, the poorer statistical region will dominate the image noise.

There are different methods to obtain multienergy measurements: (1) scan with two distinctive energy spectra, (2) detect photon energy according to penetration depth at the detector, and (3) photon counting. Photon counting provides clean spectra separation and an adjustable energy separation point for balancing photon statistics.

(A) Improved accuracy of CT number by performing better beam-hardening correction. This allows quantitative studies to be performed on head images. One of the key applications for this feature is the perfusion study. As is well known in the art, perfusion studies measure the cerebral blood volume, cerebral blood flow, and mean transit time to distinguish salvageable tissue from infarcted tissues. The measurement is performed by constantly monitoring the CT number changes in contrast-enhanced brain studies. When the accuracy of the CT number is improved, the accuracy of the perfusion measurement also improves.

(B) Improved gray-white matter contrast by performing Compton and photoelectric decomposition. It is known in the art that one performance parameter for CT head scans is the differentiation between the gray and white matter in the brain. The probability of photoelectric interaction, $P_{Photoelectric}$ is proportional to the cubic of the atomic number, Z. Consequently, tissues with small differences in atomic numbers result in greater difference in the probabilities of photoelectric effects. This, in turn, results in different absorption of x-ray photons and leads to greater contrast between different tissues.

(C) Reduced image artifacts by improving beam-hardening corrections for bone. For head scans, bone presents a source of error in accurately estimating the projections. This leads to shading and streaking artifacts, as well as CT number inaccuracy. By utilization of multiple energies and BMD, the beam-hardening effect in heads and necks of patients can be reduced or eliminated, depending on the accuracy of BMD. This leads to reduced image artifacts and better CT number accuracy.

(D) Ability to perform tissue characterization. Using the principle of BMD, there is an increased probability that different diseased tissues can be classified and separated. The ability to discriminate between brain tissues can be used to identify, measure, diagnose, and monitor therapy for brain diseases such as Multiple Sclerosis (MS) and Alzheimer's Disease (AD). The size and number of white matter lesions in the brain can be measured using MECT 10. MECT 10 results in improved spatial resolution over traditional Magnetic Resonance Imaging (MRI) measurements and will avoid intensity and shape scaling artifacts present in MRI scans. The detection and staging of Alzheimer's Disease (AD) may also be performed through automated and semiautomated quantitative analysis of MECT. Using MECT 10 to quantitatively measure the volume of brain atrophy in global brain structures (e.g. CSF, gray/white matter, intracranial cavity) or in brain substructures (e.g. ventricles, lateral ventricles, hippocampus, amygdala, Entorhinal Cortex) provides highly accurate AD clinical measurement tools. Using volume measurements of brain structures, it is possible to discriminate between normal subjects, individuals with Mild Cognitive Impairment, and individuals with AD. The stage of the disease is assessed with either a single scan or by utilizing multiple scans over time and measuring changes in the volume of brain structures.

(E) Improved detection and classification of cancerous lesions. Using the differential attenuation characteristics of the normal and abnormal tissue (such as cancerous and non-cancerous lesions) for different energy spectrums of x-rays in MECT 10, smaller abnormal nodules in the brain can be detected. In addition, classification of the detected abnormal tissue as cancerous or non-cancerous lesions and staging of the cancerous lesions is enabled.

(F) Tagging ligands with affinity and specificity to specific brain receptors, such as dopamine or serotonin receptors of the Central Nervous System (CNS), with media containing ions of elements detectable by CT. MECT enhances the detection of the contrast-enhancing media that binds to neurotransmitters or other compounds with high affinity and selectivity for specific receptors and therefore enables the diagnosis of chemical imbalances and/or neuronal dysfunction. This can be extended from diagnosis to prognosis and/or treatment. A physician can follow the effectiveness of therapeutic drugs, by labeling the drugs targeting specific receptors with the aforementioned ligands containing contrast-agent compounds. MECT 10 enhances the detection of the labeled drug and thus enables monitoring of the effectiveness of a treatment. Furthermore, different contrast agent compounds can be used in tagging the drug molecules and the receptor and/or neurotransmitter ligands. In this embodiment, MECT 10 is used in discriminating between the different contrast agents and thus enabling a simultaneous monitoring of the drug distribution and the drug"s effect on the kinetics of the targeted receptors and/or the distribution and concentration of the neurotransmitters. More accurate monitoring of drug delivery and efficacy may lead to shorter drug development cycles.

(G) MECT 10 in combination with the use of contrast agents, which tag antibodies and/or other targeting agents of specific tumors, have the potential to enhance the differentiation between tumor and normal tissue, and thus improve diagnosis. Again this application can be extended to treatment and/or prognosis. Drug delivery systems could also be bound to tumor-specific ligands. Improved image quality and sensitivity achieved with MECT, has the potential of imaging the distribution of the drug delivery systems. In one embodiment, the drug delivery systems is activated by x-ray and/or by other means in releasing their therapeutic content in a very localized and precise manner enabled by MECT.

(H) MECT 10 enables better plaque characterization when used in scanning carotid arteries. In some clinical practice utilizing a conventional CT scanner, although the conventional CT scanner is capable of detecting the presence of plaques in the carotid arteries, it is often difficult and/or impossible to differentiate the plaques in terms of stable and unstable plaques. By using BMD, the characteristics of the plaques can be identified and proper treatments can be rendered.

(I) MECT 10 enables better visualization of concussion of the supporting structures in the neck and fracture of the bones of the head and neck, such as in sports injuries.

In some clinical practice utilizing a conventional CT scanner, although the conventional CT scanner is capable of detecting the concussion and fractures in the neck and head, it is often difficult to differentiate the normal variations in the structure from certain injuries such as micro-fractures and tear of cartilage. By using BMD and providing a bone image with soft tissues removed, head and neck injuries can be better identified and proper treatments can be rendered.

(K) MECT 10 enables better detection of abnormal growth on bones such as metastatic bone lesions in the neck and skull. In some clinical practice utilizing a conventional CT scanner, although the conventional CT scanner is capable of detecting the concussion and fractures in the neck and head, it is often difficult to differentiate the normal variations in the structure from certain injuries such as micro-fractures and tear of cartilage. By using BMD and providing a bone image with soft tissues removed, abnormal growth on bones of the neck and head can be better identified and proper treatments can be rendered.

While the invention has been described in terms of various specific embodiments, those skilled in the art will recognize that the invention can be practiced with modification within the spirit and scope of the claims.

The invention claimed is:

1. A method for obtaining data, said method comprising:
   scanning at least one of a head of a patient and a neck of the patient with a Multi-Energy Computed Tomography (MECT) system, the MECT including an x-ray source rotatable about the patient, the MECT configured to be responsive to different x-ray spectra associated with Compton scatter and photoelectric effect and within an energy region associated with medical computed tomography (CT);
   acquiring, from said scanning, first image data including attenuations from a Compton process and second image data including attenuations from a photoelectric process; and
   representing a material within the acquired image data using at least one of a density of a first reference material and a density of a second reference material.

2. A method in accordance with claim 1 wherein said scanning comprises scanning a head of a patient with a Multi-Energy Computed Tomography (MECT) system to acquire data allowing computation of the cerebral blood volume of the patient.

3. A method in accordance with claim 2 wherein said scanning further comprises scanning a head of a patient with a Multi-Energy Computed Tomography (MECT) system to allow computation of the cerebral blood flow of the patient.

4. A method in accordance with claim 3 further comprising calculating a mean transit time of the cerebral blood flow based on the cerebral blood flow data and the cerebral blood volume data.

5. A method in accordance with claim 1 wherein said scanning comprises scanning a head of a patient with a Multi-Energy Computed Tomography (MECT) system to acquire data allowing computation of the cerebral blood flow of the patient.

6. A method in accordance with claim 1 further comprising performing a Compton and photoelectric decomposition of the acquired data to provide an improved gray-white matter contrast in the brain.

7. A method in accordance with claim 1 further comprising performing a Basis Material Decomposition (BMD) of the acquired data to characterize a plaque in an carotid artery.

8. A method in accordance with claim 1 further comprising monitoring a CT number change in a contrast-enhanced brain study to provide improved CT number accuracy.

9. A method in accordance with claim 1 further comprising performing a Basis Material Decomposition (BMD) of the acquired data to facilitate a reduction in image artifacts.

10. A method in accordance with claim 1 further comprising performing a Basis Material Decomposition (BMD) of the acquired data to measure a size and number of white matter lesions.

11. A method in accordance with claim 1 further comprising performing a Basis Material Decomposition (BMD) of the acquired data to measure a volume of brain atrophy in a global brain structure.

12. A method in accordance with claim 1 further comprising performing a Basis Material Decomposition (BMD) of the acquired data to measure a volume of brain atrophy in at least one brain substructure.

13. A method in accordance with claim 1 further comprising performing a Basis Material Decomposition (BMD) of the acquired data to discriminate between a Mild Cognitive Impairment condition of the patient and an Alzheimer's Disease (AD) condition of the patient.

14. A method in accordance with claim 1 wherein said scanning comprises scanning at least one of a head and a neck of a patient with a Multi-Energy Computed Tomography (MECT) system to acquire data including a location of a tagging ligand.

15. A method in accordance with claim 1 wherein said scanning comprises scanning at least one of a head and a neck of a patient with a Multi-Energy Computed Tomography (MECT) system to acquire data regarding a detection of a labeled drug.

16. A method in accordance with claim 1 wherein said scanning comprises scanning at least one of a head and a neck of a patient with a Multi-Energy Computed Tomography (MECT) system to acquire data regarding a location of a tagged ligand with an affinity to a specific labeled drug's receptors, and a detection of the specific labeled drug to simultaneously monitor the labeled drug's distribution and the drug's effect on the kinetics of the receptors.

17. A method in accordance with claim 1 wherein said scanning comprises scanning a head of a patient with a Multi-Energy Computed Tomography (MECT) system to acquire data regarding a location of a tagged ligand with an affinity to a neurotransmitter released by a specific labeled drug's receptors, and a detection of a labeled drug to simultaneously monitor the labeled drug's distribution and a concentration of the neurotransmitter.

18. A method in accordance with claim 1 wherein said scanning comprises scanning at least one of a head and a neck of a patient with a Multi-Energy Computed Tomography (MECT) system to acquire data regarding a targeting agent of a tumor.

19. A method in accordance with claim 1 wherein said scanning comprises scanning at least one of a head and a neck of a patient with a Multi-Energy Computed Tomography (MECT) system to acquire data regarding a targeting agent of a tumor wherein the targeting agent comprises a tumor-specific ligand.

20. A method in accordance with claim 1 further comprising classifying tissue as cancerous and non-cancerous based upon the acquired data.

21. A method in accordance with claim 1 wherein said scanning comprises scanning at least one of a head and a neck of a patient with a Multi-Energy Computed Tomography (MECT) system to provide an improved detection of concussion of supporting structures in the neck and fracture of the bones in the head and neck.

22. A method in accordance with claim 1 wherein said scanning comprises scanning at least one of a head and a neck of a patient with a Multi-Energy Computed Tomography (MECT) system to provide an improved detection of abnormal growth on the bones of the head and neck.

23. A Multi-Energy Computed Tomography (MECT) System configured to be responsive to different x-ray spectra associated with Compton scatter and photoelectric effect, the MECT comprising:
   a radiation source rotatable about a patient;
   a radiation detector; and
   a computer coupled to said radiation source and said radiation detector, said computer configured to:
      receive first image data regarding a first scan at a first energy spectrum, the scan being a scan of a head of the patient, the first image data including attenuations from a Compton process;
      receive second image data regarding a second scan at a second energy spectrum, the second scan being a scan of the head, wherein the first energy spectrum and the second energy spectrum are within an energy region associated with medical computed tomography (CT), the second image data including attenuations from a photoelectric process;
      generate an image of at least one of a cerebral blood volume of the patient and a cerebral blood flow of the patient using the first and second image data, wherein a material within at least one of the cerebral blood volume and the cerebral blood flow is represented using at least one of a density of a first reference material and a density of a second reference material; and
      calculate a mean transit time of the cerebral blood flow based on the received data.

24. A MECT system in accordance with claim 23 wherein said computer further configured to perform a Compton and photoelectric decomposition of the received data to provide improved gray-white matter contrast in the brain.

25. A MECT system in accordance with claim 23 wherein said computer further configured to perform a Basis Material Decomposition (BMD) of the received data to measure a volume of brain atrophy in a global brain structure.

26. A MECT system in accordance with claim 23 wherein said computer further configured to perform a Basis Material Decomposition (BMD) of the received data to discriminate between a Mild Cognitive Impairment condition of the patient and an Alzheimer's Disease (AD) condition of the patient.

27. A Multi-Energy Computed Tomography (MECT) System configured to be responsive to different x-ray spectra associated with Compton scatter and photoelectric effect, the MECT comprising:
   a radiation source rotatable about a patient;
   a radiation detector; and
   a computer coupled to said radiation source and said radiation detector, said computer configured to:
      receive first image data regarding a first scan at a first energy spectrum, the scan being a scan of at least one of a head of the patient and a neck of the patient, the first image data including attenuations from a Compton process;
      receive second image data regarding a second scan at a second energy spectrum, the second scan being a scan of the at least one of the head and the neck, the second image data including attenuations from a photoelectric process;
      represent a material within the received data using at least one of a density of a first reference material and a density of a second reference material; and
      generate a location of a tagging ligand based upon the represented material.

28. A Multi-Energy Computed Tomography (MECT) System configured to be responsive to different x-ray spectra associated with Compton scatter and photoelectric effect, the MECT comprising:
   a radiation source rotatable about a patient;
   a radiation detector; and
   a computer coupled to said radiation source and said radiation detector, said computer configured to:
      receive first image data regarding a first scan at a first energy spectrum, the scan being a scan of at least one of a head of the patient and a neck of the patient, the first image data including attenuations from a Compton process;
      receive second image data regarding a second scan at a second energy spectrum, the second scan being a scan of the at least one of the head and the neck, wherein the first energy spectrum and the second energy spectrum are within an energy region associated with medical computed tomography (CT), the second image data including attenuations from a photoelectric process;
      represent a material within the received data using at least one of a density of a first reference material and a density of a second reference material; and
      detect a labeled drug based upon the represented material.

29. A Multi-Energy Computed Tomography (MECT) System configured to be responsive to different x-ray spectra associated with Compton scatter and photoelectric effect, the MECT comprising:
   a radiation source rotatable about a patient;
   a radiation detector; and
   a computer coupled to said radiation source and said radiation detector, said computer configured to:

receive first image data regarding a first scan at a first energy spectrum, the scan being a scan of a head of the patient, the first image data including attenuations from a Compton process;

receive second image data regarding a second scan at a second energy spectrum, the second scan being a scan of the head, wherein the first energy spectrum and the second energy spectrum are within an energy region associated with medical computed tomography (CT), the second image data including attenuations from a photoelectric process;

represent a material within the received data using at least one of a density of a first reference material and a density of a second reference material;

generate a location of a tagged ligand with an affinity to a neurotransmitter released by a specific labeled drug's receptors based upon the represented material; and detect a labeled drug based upon the received data to simultaneously monitor the labeled drug's distribution and a concentration of the neurotransmitter.

30. A Multi-Energy Computed Tomography (MECT) System configured to be responsive to different x-ray spectra associated with Compton scatter and photoelectric effect, the MECT comprising:

a radiation source rotatable about a patient;
a radiation detector; and
a computer coupled to said radiation source and said radiation detector, said computer configured to:
receive first image data regarding a first scan at a first energy spectrum, the scan being a scan of a head of the patient, the first image data including attenuations from a Compton process;
receive second image data regarding a second scan at a second energy spectrum, the second scan being a scan of the head, wherein the first energy spectrum and the second energy spectrum are within an energy region associated with medical computed tomography (CT), the second image data including attenuations from a photoelectric process; and
perform a Basis Material Decomposition (BMD) of the received data to characterize a plaque in a carotid artery, wherein performing a BMD comprises representing a material within the received data using at least one of a density of a first reference material and a density of a second reference material.

31. A Multi-Energy Computed Tomography (MECT) System configured to be responsive to different x-ray spectra associated with Compton scatter and photoelectric effect, the MECT comprising:

a radiation source rotatable about a patient;
a radiation detector; and
a computer coupled to said radiation source and said radiation detector, said computer configured to:
receive first image data regarding a first scan at a first energy spectrum, the scan being a scan of a head of the patient, the first image data including attenuations from a Compton process;
receive second image data regarding a second scan at a second energy spectrum, the second scan being a scan of the head, wherein the first energy spectrum and the second energy spectrum are within an energy region associated with medical computed tomography (CT), the second image data including attenuations from a photoelectric process;
represent a material within the received data using at least one of a density of a first reference material and a density of a second reference material; and
classify tissue as cancerous and non-cancerous based upon the represented material.

* * * * *

UNITED STATES PATENT AND TRADEMARK OFFICE
CERTIFICATE OF CORRECTION

PATENT NO. : 7,627,078 B2  Page 1 of 1
APPLICATION NO. : 10/065689
DATED : December 1, 2009
INVENTOR(S) : Hsieh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 535 days.

Signed and Sealed this

Second Day of November, 2010

David J. Kappos
*Director of the United States Patent and Trademark Office*